United States Patent [19]
Furukawa et al.

[11] Patent Number: 5,869,694
[45] Date of Patent: Feb. 9, 1999

[54] PROCESS FOR PREPARING 4-HYDROXY-2-PYRROLIDONE

[75] Inventors: Yoshiro Furukawa, Osaka; Yutaka Shiomi, Matsuyama; Kenichi Nagao, Amagasaki, all of Japan

[73] Assignee: Daiso Co., Ltd., Osaka, Japan

[21] Appl. No.: 973,162

[22] PCT Filed: May 14, 1996

[86] PCT No.: PCT/JP96/01259

§ 371 Date: Nov. 19, 1997

§ 102(e) Date: Nov. 19, 1997

[87] PCT Pub. No.: WO96/36603

PCT Pub. Date: Nov. 21, 1996

[30] Foreign Application Priority Data

May 19, 1995 [JP] Japan ................................. 7-121675

[51] Int. Cl.⁶ .............................................. C07D 207/273
[52] U.S. Cl. ............................................................ 548/544
[58] Field of Search ............................................... 548/544

[56] References Cited

FOREIGN PATENT DOCUMENTS

| 62721 | 9/1973 | Japan . |
| 183756 | 11/1982 | Japan . |
| 176564 | 8/1986 | Japan . |
| 174957 | 7/1988 | Japan . |

*Primary Examiner*—Robert W. Ramsuer
*Attorney, Agent, or Firm*—Jacobson, Price, Holman & Stern, PLLC

[57] ABSTRACT

A improved process for preparing 4-hydroxy-2-pyrrolidone of the formula

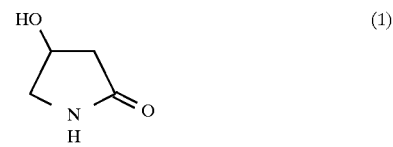

(1)

which is characterized in reacting a 4-halogeno-3-hydroxybutyrate and an alkali metal or alkaline earth metal azide, to produce a 4-azido-3-hydroxybutyrate and hydrogenating an azide group of the ester compound and then cyclizing a hydrogenated compound. 4-Hydroxy-2-pyrrolidone is useful for an intermediate of medicines and agricultural chemicals.

7 Claims, No Drawings

PROCESS FOR PREPARING 4-HYDROXY-2-PYRROLIDONE

This application is a 371 of PCT/JP96/01259 filed May 14, 1996.

FIELD OF ART

This invention relates to an improved process for preparing 4-hydroxy-2-pyrrolidone useful as an intermediate for medicines, agricultural chemicals, etc.

BACKGROUND OF ART

4-Hydroxy-2-pyrrolidone is used as an intermediate for medicines, agricultural chemicals, etc. The following processes for preparing it are known. These are a process for preparing it from a 4-chloro-3-hydroxybutyrate and ammonia [Japanese Patent Publication No. 183756/1982, Tetrahedron Lett., 41,5603(1985), Japanese Patent Publication No. 176564/1986], a process for preparing it from a 4-chloro-3-hydroxybutyrate and benzylamine (Japanese Patent Publication No. 45360/1989), a process for preparing it from a cyclobutanone derivative and optically active α-methylbenzylamine (Synthetic Comm., 21,693(1991), a process for preparing it from 3,4-epoxibutyramide and optically active α-methylbenzylamine (J. Chem. Research(s), 376, 1990), a process for preparing it by heating and dehydrating 4-amino-3-hydroxybutyric acid (abbreviated to GABOB hereinafter) [Tetrahedron Lett., 21,2443(1980), J. Org. Chem., 19,1–589(1954)], a process for preparing it from optically active GABOB and hexamethyldisilazane (Synthesis, 1978, 614), a process for preparing it from optically active 4-hydroxyproline (Japanese Patent Publication No. 250352/1988) and a process for preparing it from a 4-bromo crotonic acid ester [J. Org. Chem., 44,2798(1979)].

These processes, however, have following disadvantages industrially: The process from a 4-chloro-3-hydroxybutyrate and ammonia produces many kinds of by-products and it is difficult to achieve high yield. The process from benzylamine or α-methylbenzylamine needs debenzylation or demethybenzyllation procedure after constructing a pyrrolidone skeleton and this procedure is so troublesome as it uses an alkali metal in liquid ammonia at low temperature. The process by heating and dehydrating GABOB is low in the yield and in case using an optically active compound, the racemization occurs. The process from optically active GABOB and hexamethyldisilazane is high in the yield, but the hexamethyldisilazane is expensive and the process needs desilylation procedure after constructing pyrrolidone skeleton. The process from optically active 4-hydroxyproline or a 4-bromo crotonic acid ester comprises many steps, and it is not practical. Therefore, a more efficient process for preparing 4-hydroxy-2-pyrrolidone was desired.

DISCLOSURE OF INVENTION

The present inventors engaged extensively in solving the above problems, and found a novel process for preparing the above objective compound from a 4-halogeno-3-hydroxybutyrate and an alkali metal or alkaline earth metal azide.

This invention relates to a process for preparing 4-hydroxy-2-pyrrolidone of the formula

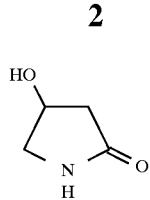

by reacting a 4-halogeno-3-hydroxybutyrate of a formula

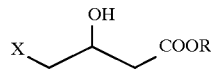

wherein X is a halogen, and R is an $C^1$–$C^4$ alkyl, and an alkali metal or alkaline earth metal azide, to produce a 4-azido-3-hydroxy-butyrate of a formula

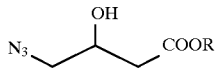

wherein R is the same as defined above, and then by hydrogenating an azide group of the ester compound in the presence of catalyst and by cyclizing a hydrogenated compound.

BEST MODE OF PRESENT INVENTION

The present invention is explained in detail by showing the reaction scheme.

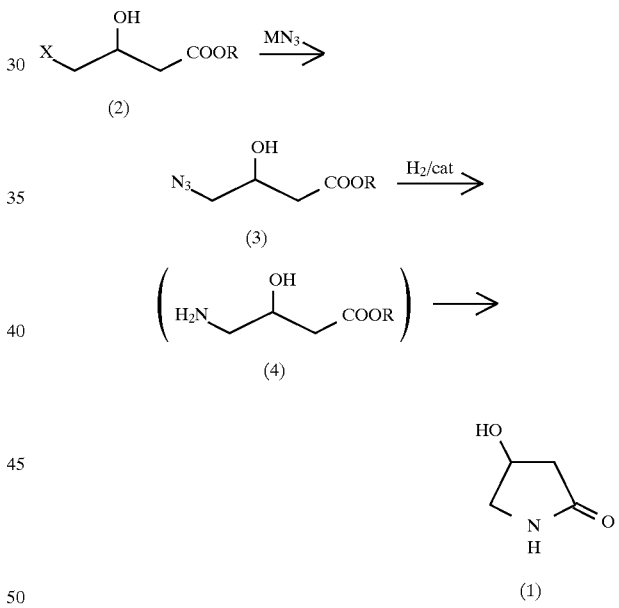

Examples of 4-halogeno-3-hydroxybutyrates of formula (2) used as a starting material are methyl 4-chloro-3-hydroxybutyrate, ethyl 4-chloro-3-hydroxybutyrate, isopropyl 4-chloro-3-hydroxybutyrate, butyl 4-chloro-3-hydroxybutyrate, t-butyl 4-chloro-3-hydroxybutyrate, methyl 4-bromo-3- hydroxybutyrate, ethyl 4-bromo-3-hydroxybutyrate, isopropyl 4-bromo-3-hydroxybutyrate, butyl 4-bromo-3-hydroxybutyrate, and t-butyl 4-bromo-3-hydroxybutyrate.

Several processes of these starting materials are proposed, and these materials can be prepared by the following known processes: e.g. a process by reacting epichlorohydrin, carbon monoxide and an alcohol (Japanese Patent Publication No. 183749/1982), and a process by reducing a gamma-halo acetoacetate prepared from diketone, a halogen and an alcohol (Japanese Patent Publication No. 157747/1983).

A 4-azido-3-hydroxybutyrate (formula (3)) is prepared by reacting the above 4-halogeno-3-hydroxybutyrate with an alkali metal or alkaline earth metal azide in a solvent. The solvents are a dipolar aprotic solvent: such as N,N-dimethylformamide, dimethyl sulfoxide, sulfolane, hexamethylphosphoramide, etc.; an ester: such as ethyl acetate, butyl acetate, etc.; an ether: such as tetrahydrofuran, 1,4-dioxane, 1,2-dimethoxyethane, diglyme, triglyme, diethylene glycol monomethyl ether, etc.; a ketone: such as acetone, methyl ethyl ketone, methyl isobutyl ketone, etc.; a nitrile: such as acetonitrile etc.; an alcohol: such as methanol, ethanol, isopropanol, t-butanol, ethylene glycol monoethyl ether etc.; water; and a mixture of these solvents.

Examples of alkali metal or alkaline earth metal azides are lithium azide, sodium azide, potassium azide, calcium azide, ballium azide, etc. Sodium azide is preferable as it is easily available. The amount of the azide is 1–3 moles per 1 mole of a 4-halogeno-3-hydroxybutyrate, preferable 1 to 2 moles. The excess amount of the azide does not affect the yield, but it is not economical.

The reaction is carried out from room temperature to refluxing temperature of the solvent. When the reaction temperature is too low, it is not practical as the reaction rate is significantly affected.

This reaction proceeds without any reaction promoter, but is promoted in the presence of dimethylaminopyridine; an iodated compound: such as cesium iodide, sodium iodide, and potassium iodide; a quaternary ammonium salt: such as tetrabutylammonium chloride; trimethylammonium bromide; or a crown ether: such as 18-crown-6, etc. Such a reaction promoter is added 0.01 to 0.3 moles per a 4-halogeno-3-hydroxybutyrate.

A 4-azido-3-hydroxybutyrate thus obtained (formula(3)) is subjected to catalytic hydrogenation under hydrogen atmosphere in a solvent to produce a 4-amino-3-hydroxybutyrate (formula(4)) and the compound is immediately cyclized to give 4-hydroxy-2-pyrrolidone (formula (1)).

The solvents are an ester: such as ethyl acetate, butyl acetate, etc.; an ether: such as tetrahydrofuran, 1,4-dioxane, 1,2-dimethoxyethane, etc.; a ketone: such as acetone, methyl ethyl ketone, methyl isobutyl ketone, etc.; an alcohol: such as methanol, ethanol, isopropanol, t-butanol, etc.; water; and a mixture of these solvents.

Catalysts are not limited as far as the catalysts are commonly used in the reaction of this kind, and they are preferably a metal catalyst: such as palladium, platinum, etc.; further preferably palladium in view of the yield and economy. Especially about 5–10% palladium-carbon powder is better. The amount of the catalyst is 0.5–50 weight percent per a raw material. The reaction is usually carried out at room temperature under the atmosphere. 4-Hydroxy-2- pyrrolidone thus prepared is prepared in the good yield and in the high purity by usual purification, such as recrystallization. The reduction and cyclization reaction of a 4-azido-3-hydroxybutyrate (formula(3)) is usually under neutral conditions, and is also possible under basic conditions. On the other hand, when it is carried out under acidic conditions, an alkyl 4-amino-3-hydroxybutyrate hydrochloride is produced, and then the reaction ceases at this stage without cyclization. Thus 4-hydroxy-2-pyrrolidone as desired is not obtained (Acta. Chem.Scand., B 37,341 (1983)). The hydrochloride is treated with a base to be cyclized to produce 4-hydroxy-2-pyrrolidone. By a catalytic hydrogenation of 4-azido-3-hydroxybutyric acid instead of a 4-azido-3-hydroxybutyrate there is also obtained 4-amino-3-hydroxybutyric acid, but there is not obtained a cyclized compound, 4-hydroxy-2-pyrrolidone (see Japanese Patent Publication No. 174957/1988).

In case of using an optically active 4-halogeno-3-hydroxybutyrate as a starting material, there is obtained optically active 4-hydroxy-2-pyrrolidone. For example, by using a (S)-4-chloro-3-hydroxybutyrate, there is obtained (S)-4-hydroxy-2-pyrrolidone. The same is applied to a (R)-compound. By using a compound with high optical purity, there is obtained a pyrrolidone with high optical purity without the marked racemization on the reaction.

EXAMPLE

The pr esent invention is explained by the following examples, but it is not limited to these examples.

Example 1

To a mixture of ethyl (S)-4-chloro-3-hydroxybutyrate (1 93 g, 1.16 mol, optical purity:98.5% ee) and N,N-dimethylformamide (1.4 Lit.) is added sodium azide (151 g, 2.32 mol) and the mixture was stirred at 100°–110° C. for 2 hours. After cooling N,N-dimethylformamide was distilled off and to the residue was added water (1 Lit.). The mixture was extracted with ethyl acetate and the extract was dried over magnesium sulfate. By distillation off ethyl acetate under vacuo, there is obtained ethyl (S)-4-azido-3-hydroxybutyrate as a crude product (206 g). Then the crude product was dissolved in methanol (1 Lit.) and to it 5% palladium-carbon (10 g) was added. The mixture was stirred for 17 hours at room temperature under a hydrogen atmosphere. After the reaction was over, palladium-carbon was filtered off and the solvent was distilled off under vacuo. The resulting product was recrystallized from acetone-water to give (S)-4-hydroxy-2-pyrrolidone (99 g, 0.98 mol, yield:84%) as a colorless crystalline solid. Optical purity:98.3% ee, Specific rotation:$[\alpha]D^{22}$ –57.6°(c=1.00, $H_2O$).

Example 2

Lithium azide (1.8 g, 37 mmol) was added to a mixture of methyl 4-chloro-3-hydroxybutyrate (33 mmol) and N,N-dimethylformamide (40 ml) and the mixture was stirred at 80°–90° C. for 7 hours. And followed by the same procedure as in example 1, there was obtained 4-hydroxy-2-pyrrolidone (2.6 g, 26 mmol, yield:79%).

Example 3

To a mixture of methyl 4-chloro-3-hydroxybutyrate (5 g, 33 mmol), and methyl isobutyl ketone (40 ml) are added sodium azide (2.3 g, 36 mmol) and 4-dimethylaminopyridine (403 mg, 3.3 mmol) and the mixture was refluxed under stirring for 11 hours. After cooling the salt was filtered off and the solvent was distilled off under vacuo and there was obtained methyl 4-azido-3-hydroxybutyrate (5.5 g) as a crude product. And followed by the same procedure as in example 1, there was obtained 4-hydroxy-2-pyrrolidone (2.3 g, 23 mmol, yield:70%). When the above reaction was carried out in the absence of 4-dimethylaminopyridine, it took more than 120 hours to detect the disappearance of the starting materials on gas chromatography.

EFFECT OF INVENTION

According to this invention, 4-hydroxy-2-pyrrolidone is obtained by a few steps, in the high yield, economically and with almost no by-products. By using a starting material with high optical purity, 4-hydroxy-2-pyrrolidone with high optical purity is obtained without the marked racemization.

We claim:

1. A process for preparing 4-hydroxy-2-pyrrolidone of the formula

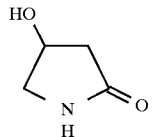 (1)

which is characterized in reacting a 4-halogeno-3-hydroxybutyrate of a formula

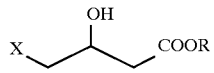 (2)

wherein X is a halogen, and R is an $C^1$–$C^4$ alkyl, with an alkali metal or alkaline earth metal azide, to produce a 4-azido-3-hydroxybutyrate of a formula

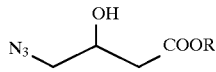 (3)

wherein R is the same as defined above, and hydrogenating an azide group of the ester compound (3) in the presence of catalyst and then cyclizing a hydrogenated compound.

2. The process of an optically active 4-hydroxy-2-pyrrolidone claimed in claim 1 characterized in using an optically active 4-halogeno-3-hydroxybutyrate as a starting material.

3. The process of 4-hydroxy-2-pyrrolidone claimed in claim 1 characterized in using a compound of formula (2) in which X is chlorine atom or bromine atom.

4. The process of 4-hydroxy-2-pyrrolidone claimed in claim 1 characterized in using a compound (2) in which R is methyl or ethyl.

5. The process of 4-hydroxy-2-pyrrolidone claimed in claim 1 characterized in reacting a compound (2) with an alkali metal or alkaline earth metal azide in the presence of a reaction promoter.

6. The process of 4-hydroxy 2-pyrrolidone claimed in claim 5 characterized in reacting in the presence of N,N-dimethylaminopyridine as a promoter.

7. The process of 4-hydroxy 2-pyrrolidone claimed in claim 1 characterized in using sodium azide as a alkali metal azide.

* * * * *